United States Patent [19]

Briggs

[11] Patent Number: 4,564,598
[45] Date of Patent: Jan. 14, 1986

[54] LIMITED VOLUME METHOD FOR PARTICLE COUNTING

[75] Inventor: Jonathan Briggs, Palo Alto, Calif.

[73] Assignee: Syntex (U.S.A.) Inc., Palo Alto, Calif.

[21] Appl. No.: 397,285

[22] Filed: Jul. 12, 1982

[51] Int. Cl.[4] .................... G01N 33/54; G01N 21/64; G01N 33/50

[52] U.S. Cl. .................... 436/501; 436/63; 436/172; 436/513; 436/518; 436/534; 436/805; 356/317; 356/318; 356/335; 356/379; 356/417; 250/459.1; 250/461.1; 250/461.2; 422/73

[58] Field of Search ............... 436/63, 172, 501, 513, 436/518, 519, 531, 534, 547, 805, 800; 356/317, 318, 417, 335, 379; 250/458.1, 459.1, 461.1, 461.2; 422/73

[56] References Cited

U.S. PATENT DOCUMENTS 4,199,559 4/1980 Ullman et al. .................... 436/800
4,421,860 12/1983 Elings et al. .................... 356/417

OTHER PUBLICATIONS

O. Adawi and M. E. Weissman, *Biophysical Journal* (1981) 33:188a.
Journal of Immunological Methods, 47, 13–24 (1981) Miller, et al., "Usage of the Flow Cytometer-Cell Sorter".
Int. J. Immunopharmac., 3(3), 249–254 (1981) Hoffman, et al., "Immunofluorescent Analysis of Blood Cells by Flow Cytometry".
Science, 212, 1266–1267 (1981) Briggs, et al., "Homogeneous Fluorescent Immunoassay".
Proc. Natl. Acad. Sci. USA, 77(8), 4904–4908 (1980) Nicoli, et al., "Fluorescence Immunoassay Based on Long Time Correlations of Number Fluctuations".

*Primary Examiner*—Esther M. Kepplinger
*Assistant Examiner*—P. K. White
*Attorney, Agent, or Firm*—Theodore J. Leitereg; Bertram I. Rowland

[57] ABSTRACT

A method and apparatus for determining the presence of particles in a fluorescent dispersion which exceed either a predetermined fluorescence intensity or size are disclosed. The method and apparatus involve the irradiation of the dispersion with excitation light, the examination of the fluorescent light entering an optical fiber from a portion of the excited region small enough to permit only a low probability that more than one particle of interest is present in the volume during a predetermined period of time, and the measurement of the emitted fluorescence entering the fiber, substantially free of excitation light, to the extent that the fluorescence differs in intensity from that of the dispersion in the absence of the particle.

11 Claims, 1 Drawing Figure

U.S. Patent  Jan. 14, 1986  4,564,598
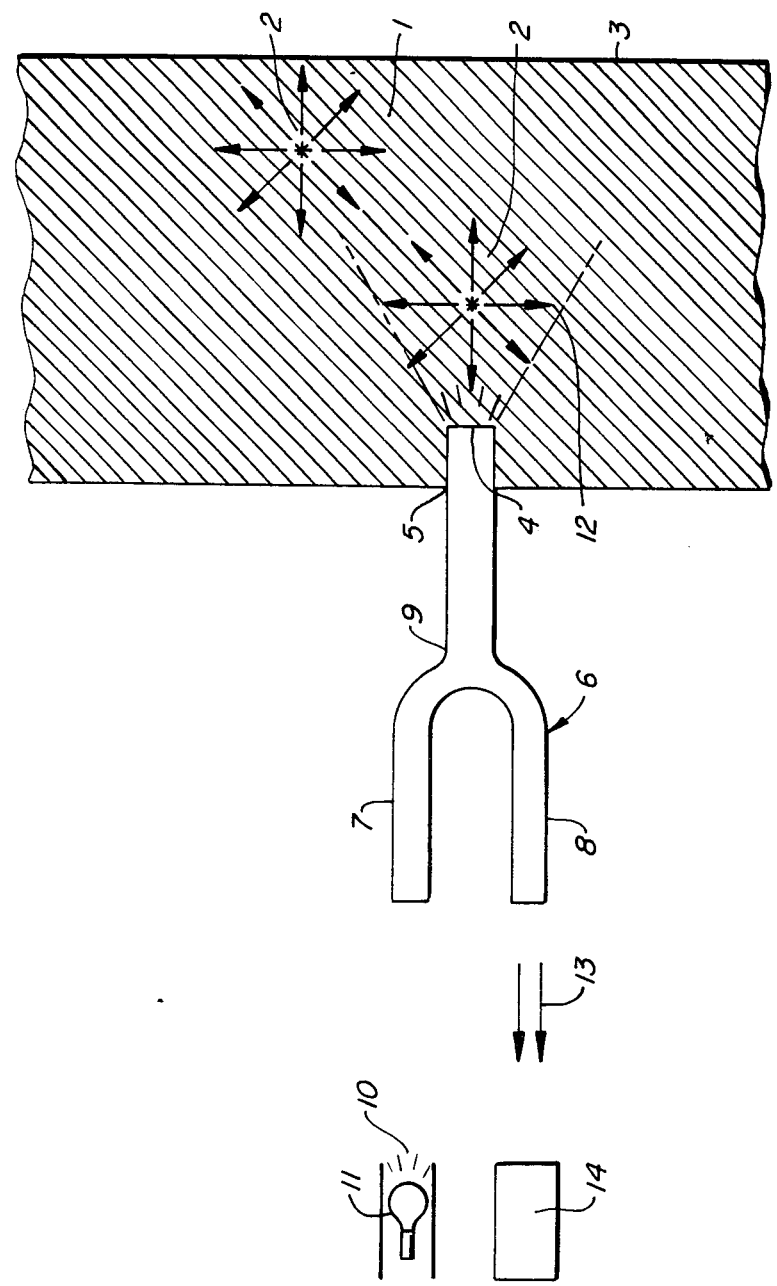
FIGURE

LIMITED VOLUME METHOD FOR PARTICLE COUNTING

BACKGROUND OF THE INVENTION

1. Field of the Invention

The counting of particles in fluid suspensions by fluorescent emission has a wide range of applicability in immunoassay techniques and in the characterization of biological materials in general. Known methods, however, require specially designed orifices, flow conduits, or sensing zones, or complex computational techniques to differentiate the particles of interest from extraneous or undesired components in the sample.

There is thus a need for an inexpensive yet accurate technique which provides a direct indication of particle presence, concentration and/or size.

2. Description of the Prior Art

The use of flow cytometers involving the carefully controlled flow of a cell suspension through a narrow flow channel is described in Miller, et al., "Usage of the Flow Cytometer-Cell Sorter," *Journal of Immunological Methods*, 47, 13–24 (1981); Hoffman, et al., "Immunofluorescent Analysis of Blood Cells by Flow Cytometry," *Int. J. Immunopharmac.*, 3(3), 249–254 (1981); Hansen, et al., U.S. Pat. No. 4,284,355, issued Aug. 18, 1981; Hansen, et al., U.S. Pat. No. 4,284,412, issued Aug. 18, 1981; Auer, et al., U.S. Pat. No. 4,284,924, issued Aug. 4, 1981; and Stevens, U.S. Pat. No. 3,275,834, issued Sept. 27, 1966.

The use of laser beams and slits to differentiate particles based on their relative size by the correlation of fluorescence fluctuations in a relatively large sample volume is described in: Briggs, et al., "Homogeneous Fluorescent Immunoassay," *Science*, 212, 1266–1267 (1981) and Nicoli, et al., fluorescence Immunoassay Based on Long Time Correlations of Number Fluctuations," *Proc. Natl. Acad. Sci. USA*, 77(8), 4904–4908 (1980).

SUMMARY OF THE INVENTION

Method and apparatus are provided for determining the presence of particles in a dispersion in relation to the detection of the presence or amount of the material of interest. An optical fiber is used to define a relatively small volume from which fluorescent light can be received and counted. The volume is related to the volume in which there is likely to be only a single particle which results in a predetermined fluctuation. By employing a variety of techniques, which allow for changes in fluorescence fluctuations in relation to the presence of an analyte in a sample, the amount of analyte present may be determined. The fluctuations are observed over a period of time in a static mode or by sampling a plurality of volumes in the sample. By comparing the observed results with results obtained with assay solutions having a known amount of analyte, the amount of analyte can be quantitatively determined.

BRIEF DESCRIPTION OF THE DRAWING

The attached drawing is a simplified schematic view of one embodiment of the apparatus of the present invention for use in detecting the presence of fluorescing particles.

DESCRIPTION OF THE SPECIFIC EMBODIMENTS

The subject invention concerns method and apparatus for determining an analyte in a sample, where the amount of analyte affects an observed pattern of fluorescence fluctuations. The analyte is a member of a specific binding pair consisting of ligand and its homologous receptor. An optical fiber is employed to receive fluorescent light from a small volume. The volume is determined by there being a high probability of their being only one particle in such volume which provides for a predetermined minimum level of change in fluorescence. One observes a plurality of such volumes, either by observing a single volume over an extended period of time, where particles diffuse in and out of the volume, or scanning a plurality of volumes either simultaneously or successively, or combinations thereof. Thus, the percentage of volumes observed which have a predetermined difference in fluorescence from a defined level can be related to the amount of analyte in the medium.

The fluctuations in fluorescence can be achieved by various combinations of particles and continuous media. For example, the combinations can include particles which fluoresce at constant intensity in a non-fluorescing solution, particles which fluoresce at varying intensity in a non-fluorescing solution, particles which are non-fluorescent in a fluorescent solution and fluorescent particles in a fluorescent solution. Furthermore, the fluorescent fluctuation may be as a result of aggregation of particles, non-fluorescent particles becoming fluorescent, or fluorescent particles becoming non-fluorescent. The particles may be comprised of polymers, both naturally occurring or synthetic, natural particles, such as virions and cells, e.g., blood cells and bacteria, or the like. Particle sizes will vary from 0.05 to $100\mu$, where synthetic particles will generally be from about $0.1\mu$ to $10\mu$ diameter.

An optical fiber is employed to define a small volume from which fluorescent light can be received and measured. The volume of interest will be comparable to or less than the volume of the assay medium divided by the total number of particles of interest present in the assay medium. In effect, this is the average volume in which a single particle of interest will be found.

The measured volume will be affected by a number of factors. One factor, will be the intensity of irradiation in the sample volume. The greater the intensity, the larger the volume which will provide the required difference in fluorescence from the base value. A second factor is whether the particles will be homogeneous or heterogeneous in the amount of fluorescence from a particle. That is, whether there is a single population of fluorescent particles or a distribution of particles having varying levels of fluorescence. This can be as a result of aggregation of fluorescent particles or particles becoming fluorescent by accretion of fluorescent molecules, or losing fluorescence by quenching, where each quenching event results in only partial quenching of a fluorescent particle. Other factors include the cross-section of the fiber, opacity of the solution at the wavelengths of interest, sensitivity of the detector, intensity of fluorescence of individual particles, etc.

Where the fluorescence of the particles is uniform, the desired volume is easily calculated. Where, however, the particle is heterogeneous, as to its effect on the observed change in fluorescence, then the calculation is more complicated. Since in an assay, there is a known concentration range or particular concentration of interest of the analyte, one can calculate the maximum number of particles which will be present in the assay medium providing a change in fluorescence greater than the threshold value in relation to the concentration range of the analyte. One can then use this value as a determination of the volume to be sampled by the optical fiber. For the purposes of the description of the subject invention, the "effective sample volume" is defined as that volume where there is a low probability of having a two-fold change in observed fluorescence over a threshold value from a base value. In its simplest form this may be considered as a low probability of finding more than one particle of interest in the effective sample volume.

The volume from which the fluorescent light is obtained is determined by the construction of the optical fiber. The shape of the volume will normally be conical. the optical fibers are typically constructed of a core region and one cladding region, whose diameters and relative refractive indices determine both the half angle of the cone and the cone's smallest diameter (at the tip of the fiber). The effective axial length is determined by the intensity of the excitation beam and the rate of drop in intensity of the excitation light with increasing axial distance from the fiber tip. This rate depends upon the half angle of the cone, with larger half angles causing greater rates of intensity drop and hence shorter effective cone lengths. Also affecting the intensity drop will be light scattering and absorption properties of the medium.

The various parameters affecting the observed signal will be chosen to insure that a reasonable threshold value is available for an effective sample volume, which will allow for discrimination against background signals. A plurality of effective volumes are measured. The different effective sample volumes may be as a result of an extended period of time which allows for diffusion of particles in and out of the effective sample volume or having a plurality of optical fibers, each one receiving signals from a non-intersecting effective sample volume. Alternatively, a dynamic system may be used where the sample flows by one or more optical fibers or one or more optical fibers move through the sample.

The amount of fluorescent light received by the optical fiber from the effective sample volume may be affected by a number of factors. The light scattering of the medium may vary, depending upon the source of the sample, as well as the reagents employed in the assay. Also, various soluble dyes may be present in the continuous aqueous medium, which will absorb light. Filters may also be employed which will cut out light outside of a predetermined wavelength range. In this way, the observed base level may be varied widely in accordance with the requirements of the assay.

The optical fiber employed for producing the effective sample volume will generally have a diameter of about 5 microns to about 500 microns more usually from about 10 microns to 100 microns. The cone half angle of the effective sample volume will generally range from about 8° to about 60°, more usually from about 10° to about 30°. The effective length of the axis will also vary significantly, generally ranging from about 0.5 to about 10 fiber diameters, more usually from about 1 to about 5 fiber diameters.

The effective sample volume is a function of both time and volume. In effect, one integrates the amount of fluorescent light received by the optical fiber over a predetermined time interval. As one measures the effective sample volume, one looks for sharp transitions which exceed the mean or normal fluctuations inherent in the background.

The effect of a particle moving through the effective volume is a rapid change with time of the number of photo-pulses (a fraction of the number of photons) observed. By various means, one can observe a burst of light or a rapid change in the number of photons during the period of time of the effective sample volume. A burst which exceeds a predetermined threshold value difference from the base value can be counted and related to whether the effective sample volume is considered to be positive or negative or in structural terms, whether a particle is deemed to be present or absent in the effective sample volume.

The "gate time" is the period of time during which photo-pulses are counted. Bursts of light, exceeding the threshold value are typically counted by instrumentation which measures the rate of change of photo-counts during consecutive gatetimes and records the number of times this rate of change exceeds a certain value. The length of the gate time will be a function of sensitivity and convenience. Since one is interested in making a large number of measurements, the gate time should be as short as possible. However, with too short a gate time, the number of photo pulses may become too few and large errors would then be introduced. Subject to these considerations, the gate time may vary over a wide range and generally will lie within the range of about 0.1 to about 100 milliseconds, more usually from about 1 to about 20 milliseconds.

The excitation light may be provided by irradiating the entire sample or a major portion of the sample with excitation light. Alternatively and preferably the excitation light may be provided by the optical fiber, so that the effective sample volume will be proportional to the volume irradiated. Since it is important that the effective sample volume be the same for each effective sample volume measured, the effective sample volume addressed by the fiber should not be intersected by walls or other mechanical intrusions.

The fluorescence originating in the effective sample volume is measured substantially free of excitation light which may result from reflection within the optical fiber device or by leakage from the excitation light source. To promote the separation of excitation from fluorescent light, fluorescers with a broad Stokes shift are preferred, particularly a shift of at least 10 nm, preferably at least 15 nm. Such separation may be further aided by measuring only the emission occurring within a wave length band which substantially excludes the excitation light. In addition, excitation light is eliminated by a filtering device positioned between the sample end of the fiber and the detector. Detection is then accomplished by any conventional means for measuring fluorescence. Discrimination between emissions above and below the predetermined level can be accomplished by utilizing a discriminating device, such that only those signals in excess of the threshold level are detected.

A particularly useful optical fiber device is the commercially available device known as a coupler, consisting of three optical fibers joined to form a bifurcated conduit with three terminal ports, conveniently referred to as an input port (into which excitation light is fed), a probe port (which is submerged in the sample)

and a detector port. In a form convenient for use in the present invention, the fibers are joined in such a manner that substantially all light entering the input port is transmitted to the probe port. Light entering the probe port (as from the fluorescent emission) may be split at the conduit juncture so that a portion will travel to the input port and a second portion to the detector port. Alternatively, a dichroic mirror can be utilized at the juncture directing substantially all of the fluorescent light to the detector port. Such devices are available from commercial suppliers, for example: Kaptron Incorporated, Palo Alto, Calif.

The fluorescence signal may be obtained by the use of any conventional fluorescing compound. Particles emitting fluorescence can be obtained by binding a fluorescing compound to the particle surface or by using particles which exist in their natural state with fluorescent components on the surface. Typical fluorescers include xanthene dyes (such as fluoresceins, rosamines and rhodamines), naphthylamines, coumarin derivatives (such as 3-phenyl-7-isocyanatocoumarin, 4-methyl-7-dimethylamino coumarin and 4-methyl-7-methoxycoumarin), stilbene derivatives (such as 4-dimethylamino-4′-isothiocyanatostilbene) and pyrenes. Descriptions of fluorescers can be found in Brand, et al., *Ann. Rev. Biochem.*, 41, 843–868 (1972) and Stryer, *Sience*, 162, 526 (1968).

By employing the above-described method in a fluorescent assay, a large number of protocols and reagents may be employed. One group of protocols will involve measuring fluorescent particles. This group can be further divided into particles which remain uniformly fluorescent, that is, there are basically two particle populations, fluorescent or non-fluorescent, or particles which involve a broad range of fluorescence, where fluoresence above a certain level is defined as a positive or negative result.

In the first embodiment to be described, the particles are uniformly fluorescent. As a result of binding of a quencher label to a particle, the particle becomes non-fluorescent. For example, fluorescent particles can be prepared having a ligand bound to the particles, which ligand is an analog of the analyte. Charcoal particles can be conjugated with anti-ligand (a receptor which specifically binds to a ligand). By combining in an assay medium, the sample containing the analyte, the ligand conjugated fluorescent particles and the anti-ligand conjugated charcoal particles, the number of charcoal particles which bind to the fluorescent particles over a predetermined time period will be determined by the amount of analyte in the medium. Thus, at times $t_1$ one examines a number of effective sample volumes and determines what percentage of these effective sample volumes result in the fluorescence being greater than the threshold value. After an interval of time, at $t_2$, one repeats the same measurement. The rate of change in the percentage of effective sample volumes being greater than the threshold value will be related to the amount of analyte in the medium. This analysis has assumed that the binding of a charcoal particle to a fluorescent particle through the intermediacy of noncovalent binding of the ligand and the anti-ligand results in complete or substantially complete quenching of the fluorescent particles. Where only a small percentage of the total fluorescence is quenched by a charcoal particle, then the analysis will be basically the same as a heterogeneous population of particles having varying fluorescence.

The heterogeneous population of fluorescent particles can come about in a number of ways. For example, one can have aggregation or agglutination of particles. For example, the analyte could be a receptor or antibody, which is polyvalent in binding sites. Fluorescent particles could be conjugated with ligand, so that the polyvalent receptor would act as a bridge between particles. In this way, the greater the amount of analyte present in the medium, the larger the number of aggregations which will result. The particle of interest could then be chosen as a particle which is an aggregation of two or more or three or more particles. Furthermore, by appropriate electronic means, one could determine the size of the aggregation, not only counting the total number of aggregations above a certain number of particles, but the number of members of each population. As the aggregation increases in size, the fluorescence of the aggregate particle will also increase, but not linearly with the increase in number of particles in the aggregation.

A second way for having a heterogeneous population has in part already been considered, where binding of quencher to a fluorescent particle only partially diminishes fluorescence. Alternatively, one could have a non-fluorescent particle, where fluorescent molecules become bound to the particle in proportion to the amount of analyte in the medium or to the number of binding sites on the particle. For example, one could have fluorescent molecules bound to an antiligand. Ligand could be bound to a non-fluorescent particle. The fluorescer conjugated antiligand would be combined with the analyte containing sample, so that the analyte could fill the binding sites of the antiligand, with the remaining binding sites being related to the amount of analyte in the sample. Upon addition of the ligand conjugated particles to the medium, the remaining fluorescent conjugated receptor would bind to the particles, providing for a distribution of particles of varying fluorescence. A threshold value of fluorescence intensity would be chosen as indicating a positive value for an effective sample volume. One would then determine the percentage of effective sample volumes which have fluorescence greater than the threshold value, either at a predetermined time interval, at equilibrium, or at two different times. In effect, one may determine a static value, that is a single value or a rate of change, where the system is distant from an equilibrium value.

Non-fluorescent particles may also include cells which have a plurality of antigens on the cell surface, there being a number of each antigen present. By employing fluorescer-labeled-antibodies to the surface antigens, the non-fluorescent cells will become fluorescent. Usually, there will be a distribution of levels of fluorescence, although in some situations it will be feasible to substantially saturate the available binding sites on the cell surface, so as to approximate only two populations, non-fluorescent cells and cells of substantially uniform fluorescence.

A third technique may also be illustrated by employing an aggregation. In this technique, non-fluorescent particles are employed, but the continuous phase is made fluorescent. In this system, the aggregation will have to be a significant percentage of the effective sample volume. Thus, when the aggregation is present in the effective sample volume, there will be a substantial diminution in the observed fluorescence. These particles, while non-fluorescent should also be substantially opaque to fluorescent light. Thus, they will create a substantial shadow, inhibiting fluorescent light from reaching the optical fiber in a volume substantially greater than the volume of the aggregation.

The above techniques are only illustrative of a few of the many types of assays available for determining analytes. These assays may be found in a number of articles and patents, a few of the patents being illustrated by U.S. Pat. Nos. 3,826,613; 3,853,987; 3,925,541; 4,061,466; 4,062,935; 4,141,965; 4,164,558; 4,256,834; 4,275,149; and 4,318,707. The description of the various methods is incorporated herein by reference, these descriptions not intended to be exhaustive, but rather illustrative of the variety of methods to which the subject invention may be applied.

A further understanding of the apparatus may be achieved by reference to the attached drawing, which illustrates an embodiment of the invention as it could be used in an assay. A liquid sample 1 containing the particles 2 in suspension is contained in a sample receiving means 3. The sample receiving means may be any vessel capable of holding the sample and receiving the tip 4 of an optical fiber 5 below the liquid surface. Vessels of small size, such as microtiter wells, are useful here.

The above apparatus is indicated for a batch system where materials are introduced manually into the sample container. Various other pieces of equipment may be employed for continuous or batch operation. For example, pipettor-diluters can be used for automatically transferring the sample and reagents in predetermined volumes. A flow tube can be employed, where the sample and reagents are mixed automatically and then passed through a tube in which the optical fiber is immersed. Various configurations can be employed which are conventional with manual or automated equipment.

The optical fiber 5 is described above in general terms, and shown in the drawing as the single (or probe) fiber of a "Y"-shaped coupler 6. The two branch fibers are an input fiber 7 and a detector fiber 8, and all three are coupled at a juncture 9. Excitation light 10 from a light source 11 is introduced into the coupler through the tip of the input fiber. The excitation light source may be any source which emits electromagnetic radiation within the absorption spectrum of the fluorescer used in the assay. A preferred light source is one emitting blue light and reading above about 400 nm. He-Cd and Ar lasers are particularly useful in this regard. With extended light sources, filters are employed to ensure that the wavelength range of excitation light is within the desired range.

The juncture 9 directs substantially all of the light from input fiber 7 to probe fiber 5 from which the light enters the liquid sample 1 through probe tip 4 to irradiate an effective sample volume 12. As already indicated other means may be used for irradiating the sample with excitation light, either as a narrow beam or including the entire sample in the light beam. With the optical fiber, the effective sample volume is a cone-shaped portion of the sample, the lateral (curved) boundary of which is determined by the structure of the optical fiber, and the axial length of which is determined by the intensity of the light source and the rate of intensity drop with increasing distance from the tip into the sample. Only a portion of the fluorescent light from the single particle shown inside the effective sample volume 12 is emitted in an appropriate direction to re-enter the probe fiber tip. This portion is then transmitted back through the probe fiber 5 to the coupler juncture 9, where it is either split equally or at some fixed ratio between input fiber 7 and detector fiber 8, such that a signal 13 is provided at the exit of the detector fiber 8 of sufficient intensity to be read by a detector 14 and distinguished from background noise. The detector is any device capable of receiving photons and converting them to a form which permits differentiation between signals of different intensities. A photomultiplier is a typical example.

The electrons emitted in one photo-pulse by a photomultiplier tube may be directed to a preamplifier discriminator which amplifies the signal, discriminates against noise originating in the photomultiplier tube and generates a well formed voltage pulse which may be counted by a digital counter. The number of photopulses per counter gate time is proportional to the intensity of light averaged over the gate time. These photopulse count values are interfaced to a computer which is programmed to detect changes in the count values, signifying a sharp fluctuation of fluorescence corresponding to the passage of a particle of interest through the effective sample volume. This is only one example of how the signal from the light detector may be digitally analysed. Alternatively, one could derive an analog signal from the detector and detect sharp transitions with a high-pass filter. Or, combinations of analog and digital techniques could be used. In any case, the frequency of fluctuations in the signal exceeding a threshold value may be interpreted to correspond to the frequency of which particles of interest are detected in the effective sample volume.

One can then determine the percentage of effective sample volumes which are deemed to be positive, that is providing fluorescence above a predetermined threshold level. One can also carry out the assays with samples having a known amount of analyte and graph the observed percentages of positive effective sample volumes against concentration of analytes. The computer will then automatically calculate the concentration of analyte in the sample based on the determination of positive effective sample volumes. This calculation may be based on a difference between percentages of positive effective sample volumes over a predetermined time interval, for a single time prior to equilibrium, or for a single time near or at equilibrium.

EXAMPLE 1

This example demonstrates the use of the present invention in counting the fluorescent particles present in a fluid suspension containing both fluorescent and nonfluorescent particles.

Polystyrene beads 0.9 micron in diameter predyed with coumarin were obtained from Polysciences, Inc., Warrington, Pa. The beads were combined with similar but undyed beads in an aqueous buffer solution containing sufficient bovine serum albumin to keep the beads in suspension and apart. Several such suspensions, each with a total of $3.5 \times 10^7$ beads per ml but with varying proportions of dyed and undyed beads were placed in 2 ml plastic cups. Each suspension was then analyzed as follows.

The single fiber end of a "Y"-shaped fiber optics coupler obtained from Kaptron, Inc., Palo Alto, Calif. (Splitter-Monitor, Model FOMS-850-P), was submerged in the suspension. The fiber had a diameter of 50 microns and produced an excitation cone with a half angle of 12° and an effective sampling volume of $1 \times 10^{-7}$ ml. Excitation light from a He-Cd laser was fed into one of the two branch fibers and, as the dyed particles diffused through the sampling volume, the portion of the fluorescence emitted from these particles which re-entered the submerged fiber end was split at the fiber juncture to transmit equal halves back along the two branch fibers. The portion traveling through the second branch fiber was then read on a high-gain EMI photomultiplier after filtering out interference within gate times of 20 milliseconds at the rate of one every 0.1 second for periods of time ranging from 50 to 500 seconds. The average number of fluorescent pulses per gate time was then determined by computer. To enhance the accuracy of the measurement, longer total sampling times were employed as the proportion of dyed particles decreased. A blank run, using no dyed beads, was made to establish the background emission level.

The results are listed in Table I, where the average number of dyed beads present in the sample, as determined by the computer, is shown versus the concentration of dyed beads, as measured by actual counting under a fluorescent microscope. The data indicate a smooth correlation.

TABLE I

TEST RESULTS: DYED VS. UNDYED BEADS

Total Bead Concentration: $3.5 \times 10^7$ beads/ml
Effective Sample Volume: $1 \times 10^{-7}$ ml
Gate Time: 20 milliseconds

| Dyed Bead Concentration ($ml^{-1}$) | Total Sampling Time (sec) | Relative Signal |
|---|---|---|
| 0 (threshold) | 200 | $2.5 \times 10^4 \pm 2.5 \times 10^{-4}$ |
| $1.7 \times 10^4$ | 500 | $8.0 \times 10^{-4} \pm 2.8 \times 10^{-4}$ |
| $6.9 \times 10^4$ | 100 | $5.2 \times 10^{-3} \pm 1.6 \times 10^{-3}$ |
| $2.8 \times 10^5$ | 100 | $1.7 \times 10^{-2} \pm 0.3 \times 10^{-2}$ |
| $1.1 \times 10^6$ | 75 | $9.3 \times 10^{-2} \pm 0.8 \times 10^{-2}$ |
| $4.4 \times 10^6$ | 50 | $2.6 \times 10^{-1} \pm 0.2 \times 10^{-1}$ |
| $1.8 \times 10^7$ | 50 | $4.6 \times 10^{-1} \pm 0.2 \times 10^{-1}$ |

EXAMPLE 2

This example demonstrates the detection of bead agglutination by use of the present invention.

The dyed beads described in Example 1 were coated with anti-immunoglobulin E (anti-IgE) and suspended in a buffer solution in a similar manner. Varying amounts of IgE were then added to several such suspensions and an analysis was performed using the fiber optics coupler and method described in Example 1.

The results are listed in Table II, where the particle count is shown to increase with an increasing quantity of IgE, reflecting the higher incidence of bright bead aggregates.

TABLE II

TEST RESULTS: BEAD AGGLUTINATION

Total Bead Concentration: $3.5 \times 10^7$ beads/ml
Effective Sample Volume: $0.5 \times 10^{-6}$ ml
Gate Time: 20 milliseconds

| IgE Concentration (ng/ml) | Relative Signal |
|---|---|
| 0.0 | $7.6 \times 10^{-2} \pm 0.9 \times 10^{-2}$ |
| 0.1 | $7.9 \times 10^{-2} \pm 1.3 \times 10^{-2}$ |
| 1.0 | $9.8 \times 10^{-2} \pm 1.0 \times 10^{-2}$ |
| 10.0 | $13 \times 10^{-2} \pm 2.0 \times 10^{-2}$ |
| 1000 | $37 \times 10^{-2} \pm 3.0 \times 10^{-2}$ |

It is evident from the above results that the subject method provides a simple accurate way for determining low concentrations of a wide variety of ligands. The subject method is readily adaptable to a wide variety of assays employing fluorescent labels. In addition, the subject method can be applied to novel protocols involving the counting of fluorescent bodies where the bodies can all have substantially the same fluorescence or can have widely varying fluorescence. The equipment is simple, can be readily automated and can provide for direct reading of the amount of analyte in the sample, based on the observed signal.

Although the foregoing invention has been described in some detail by way of illustration and example for purposes of clarity and understanding, it will be obvious that certain changes and modifications may be practiced within the scope of the appended claims.

What is claimed is:

1. A method for determining the presence of an analyte in a sample suspected of containing said analyte, said method comprising irradiating at least small predetermined effective volume of a particle-containing assay medium containing said sample with excitation light, where at least one of said particles of said medium is fluorescent and wherein said effective sample volume is defined spatially and temporally solely by means of an optical fiber in contact with said medium to have a low probability that its fluorescence intensity will fluctuate substantially from the mean fluorescence intensity value of multiple sample volumes and where the presence of said analyte results in a variation of observed fluctuations in the fluorescent intensity values obtained from a plurality of effective sample volumes of said assay medium, determining the fluorescent intensity values from a plurality of effective sample volumes employing said optical fiber to receive fluorescent light from said effective sample volumes, and deriving the amount of analyte in said sample from the number of fluctuations in said fluorescent intensity values from the mean value.

2. The method of claim 1 wherein the amount of analyte in said sample is derived by relating the number of fluctuations from the mean value to the fluctuations in an assay medium having a known amount of analyte.

3. The method of claim 1 wherein said fluctuations are as a result of aggregation of particles.

4. The method of claim 3 wherein said particles are fluorescent.

5. The method of claim 1 wherein said fluctutations are as a result of binding of fluorescer to a non-fluorescent particle.

6. The method fo claim 1 wherein said fluctuations are as result of quencher binding to a fluorescent particle.

7. The method of claim 1, 2, 3, 4, 5, or 6 wherein said effective sample volume is irradiated with light from said optical fiber.

8. The method of claim 1 wherein said sample is a physiological fluid.

9. A method for determining the presence of an analyte in a sample suspected of containing said analyte, where said analyte is a member of a specific binding pair (sbp) consisting of ligand and its homologous receptor, said method comprising irradiating, with excitation light by means of an optical fiber, an effective sample volume of an assay medium containing said sample and fluorescent particles to which are bound a plurality of a member of said sbp so that said fluorescent particles aggregate in proportion to the amount of analyte in said medium, where said effective sample volume is defined solely by said optical fiber as to size and time so that the probability of a fluctuation in the fluorescence intensity value from a threshold value greater than a predetermined value is low and where said optical fiber is contacted with said assay medium, determining the fluorescent intensity values from a plurality of effective sample volumes employing said optical fiber which receives fluorescent light from said effective sample volumes, and deriving the amount of analyte in said sample from the variation in said fluorescent intensity values from said predetermined value.

10. The method of claim 9 wherein the amount of analyte in said sample is derived by relating the variation in intensity of said effective sample volumes from said predetermined value to the variations in an assay medium having a known amount of analyte.

11. The method of claim 9 wherein said optical fiber is immersed in said assay medium.

* * * * *